US009459243B2

United States Patent
Susel et al.

(10) Patent No.: US 9,459,243 B2
(45) Date of Patent: Oct. 4, 2016

(54) ULTRASONIC TRANSDUCERS IN ASPIRATING SMOKE DETECTORS FOR TRANSPORT TIME MEASUREMENT

(71) Applicant: Honeywell International Inc., Morristown, NJ (US)

(72) Inventors: Michele Susel, Trieste (IT); Federico Cernoia, Udine (IT); Massimo Bressanutti, Sesto al reghena (IT)

(73) Assignee: LIFE SAFETY DISTRIBUTION AG, Hegnau (CH)

( * ) Notice: Subject to any disclaimer, the term of this patent is extended or adjusted under 35 U.S.C. 154(b) by 586 days.

(21) Appl. No.: 13/873,838

(22) Filed: Apr. 30, 2013

(65) Prior Publication Data

US 2014/0318218 A1    Oct. 30, 2014

(51) Int. Cl.
*G01N 33/00* (2006.01)
*G01N 29/024* (2006.01)
*G01N 29/24* (2006.01)
*G08B 17/10* (2006.01)
*G08B 29/14* (2006.01)
*G01N 15/00* (2006.01)
*G01N 11/00* (2006.01)

(52) U.S. Cl.
CPC ............ *G01N 33/007* (2013.01); *G01N 29/24* (2013.01); *G08B 17/10* (2013.01); *G08B 29/145* (2013.01); *G01N 2011/0073* (2013.01); *G01N 2015/0046* (2013.01)

(58) Field of Classification Search
CPC .................... G01F 1/7082; G01N 2011/0073; G01N 2015/0046; G01N 29/024; G01N 33/007
See application file for complete search history.

(56) References Cited

U.S. PATENT DOCUMENTS

| 7,669,457 | B2 | 3/2010 | Griffith et al. | |
|---|---|---|---|---|
| 2013/0219986 | A1* | 8/2013 | Laukkanen | G01F 1/7044 73/1.24 |
| 2013/0238138 | A1* | 9/2013 | Cole | G08B 17/10 700/275 |
| 2015/0059745 | A1* | 3/2015 | Barker | A61M 16/0066 128/203.14 |

OTHER PUBLICATIONS

System Sensor®, FAAST Fire Alarm Aspiration Sensing Technology®, product data sheet 2011©.

* cited by examiner

*Primary Examiner* — Paul West
(74) *Attorney, Agent, or Firm* — Husch Blackwell LLP

(57) ABSTRACT

A method and apparatus of determining gas transport time from an input port to first and second ultrasonic detectors in a flow conduit for an aspirated smoke detector are provided. The method includes first measuring a transit time of ambient air between the detectors. Then, a different gas is injected into the conduit, and the time of injection is stored. The transit time is measured at least intermittently between the two ultrasonic detectors until a change therein is detected. A time of detected change is subtracted from the time of injection to establish a transport time for the aspirated smoke detector.

18 Claims, 3 Drawing Sheets

ULTRASONIC TRANSDUCERS IN ASPIRATING SMOKE DETECTORS FOR TRANSPORT TIME MEASUREMENT

FIELD

The application pertains to systems and methods of using ultrasonic transducers in aspirated smoke detectors to measure transport times. More particularly, the application pertains to such systems and methods that use ultrasonic transducers to measure transit times through two different gases in an aspirating smoke detector to determine transport times.

BACKGROUND

Various configurations of aspirated smoke detectors are known to be useful in harsh environments, where maintenance can be difficult or where aesthetics matter. Several embodiments thereof are disclosed in Griffith et al., U.S. Pat. No. 7,669,457, entitled "Apparatus and Method of Smoke Detection". The '457 patent issued Mar. 2, 2010, is assigned to the assignee hereof, and is incorporated herein by reference.

When the installation of an aspirating smoke detector and associated conduit or pipe network is performed, it is necessary and required that the installer measure the transport time of the installed apparatus. This measurement is performed to verify that one of the core parts of the installation, the pipe network, has been correctly installed.

Transport time is the time for air/smoke to flow from a sampling point to the smoke sensing element in the aspirating device. The transport time will preferably not include any processing time and is specifically limited to the time it takes to transport air/smoke from the sampling point to the sensing element.

The theoretical transport time can be estimated by software tools. The installer compares software results with the measured transport time to verify that, in the real system, there are no pipe leakages, errors in setup of the device, issues with a fan, incorrect pipe assembly, etc.

The typical way that installers measure transport time in a real system is to use smoke pellets or cotton wicks to produce smoke to flow into a selected opening or hole of the pipe network connected to the aspirated detector. The transport time is measured as the time between the start of smoke inflow and the signaling of the presence of smoke at the aspirated device. The device is set to the highest level of sensibility.

The measured time is not the transport time as defined. It is the transport time plus the processing time to respond to inflowing smoke, which depends on the characteristics of the sensing element and associated alarm/filtering algorithms. The problem is that the processing time is difficult to calculate because it may vary from one test to another, due, for example, to unknown polling intervals, and, with time, due to changes in the alarm threshold. This additional time causes an inaccurate and non-reproducible determination of the transport time, affecting the verification of the system. It would be desirable to eliminate these inaccuracies.

DETAILED DESCRIPTION

Figure 1A:
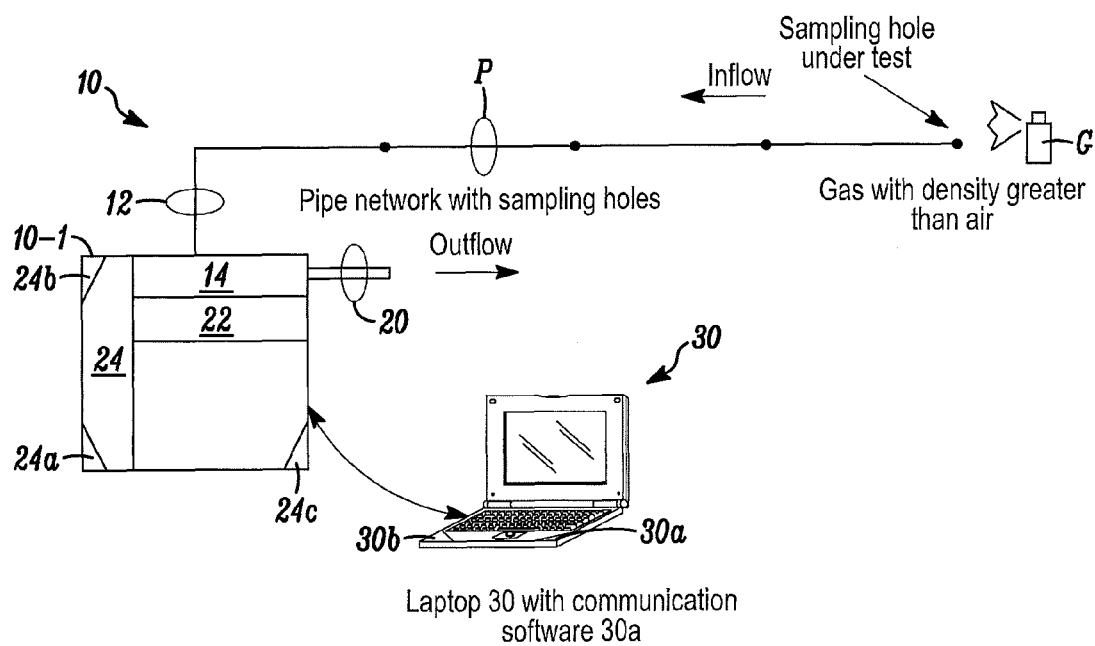
FIG. 1A illustrates a block diagram of a system in accordance herewith.

While disclosed embodiments can take many different forms, specific embodiments thereof are shown in the drawings and will be described herein in detail with the understanding that the present disclosure is to be considered as an exemplification of the principles thereof as well as the best mode of practicing the same and is not intended to limit the application or claims to the specific embodiment illustrated.

In one aspect, embodiments hereof can measure transport time without the additional processing time. The starting point is that some commercial aspirating smoke devices are equipped with ultrasonic transducers to measure the air flow of the pipe network. An internal controller measures the transit times of an ultrasonic pulse propagating along an internal path, for example, with and against the direction of the flow. A pair of ultrasonic transducers can be used for this purpose. The sampled transit times are processed by the programmable controller to obtain the transport time.

We have recognized that the transit times, which could be measured with and against the flow, are affected by the density of the flowing medium. For example, assuming the same flow speed, the transit time sampled, if the medium is air, is different from the transit time sampled if the medium is tetrafluoroethane. Using our technique, as discussed below, the transit times can be measured excluding additional processing times.

In this regard, the speed of sound c in gases is given by the Newton-Laplace equation:

$$c = \mathrm{SQRT}(K/r)$$

where:
K is a coefficient of stiffness (the modulus of bulk elasticity)
r is the density of the gas
(SQRT=square root)

Thus, the speed of sound decreases with the increasing density of the gas.

Considering that the density (r) of tetrafluoroethane is greater than air, it means that the speed of sound in this medium is lower than the speed of sound in air. As a consequence, when the tetrafluoroethane reaches the internal path of the ultrasound detectors, the transit time increases. In embodiments hereof, the transport time is established by sampling, recording, and evaluating the ultrasound transit times and detecting flow medium changes as described in more detail below.

In practice, the installer inserts a gas different from air in a sampling hole in the conduit or pipe network. The present system indicates when the gas arrives in the smoke sensing element. The interval between the arrival time and the gas insertion time is the transport time.

Figure 1B:
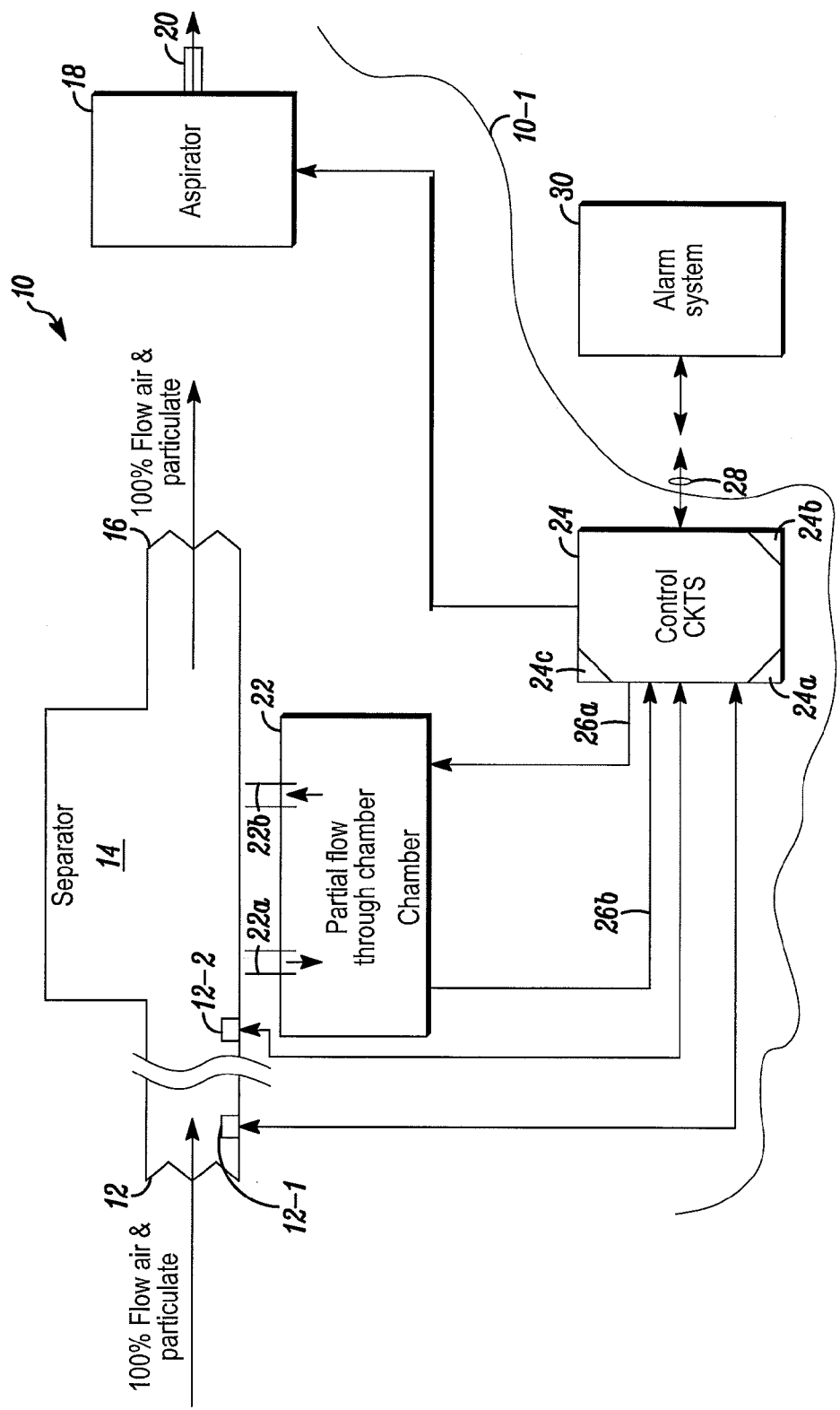
FIG. 1B illustrates additional details of the system of FIG. 1A.

FIGS. 1A and 1B illustrate an aspirated detector 10 in accordance herewith. Detector 10 is connected to a gas sample delivery pipe network P. Detector 10 is carried, at least in part in a housing 10-1.

The embodiment of FIGS. 1A and 1B has an ambient air inflow port 12, a particle separator 14, as would be understood by those of skill in the art, and an outflow port 16. The outflow from port 16 is in fluid flow communication with an aspirator 18. As a result of the pressure differential developed at separator 14, smaller, lighter particles of airborne particulate matter will be diverted from the flow from port 12 as discussed below.

Aspirator 18 can be implemented as a fan, or other element, which produces a reduced pressure at port 16, thereby drawing ambient air and associated particulate matter into port 12.

Chamber 22, a smoke detection chamber, receives, via port 22a, a partial flow of inflowing ambient air with larger particles excluded. Chamber 22 can be implemented as a photoelectric, an ionization, or both, sensing chamber without limitation. Neither the exact details of the separator 14, nor the smoke detection chamber 22, are limitations hereof.

Control circuits 24 are coupled to aspirator 18 and chamber 22. Circuits 24, which could be implemented, at least in part, with a programmed processor 24a, and associated executable control software 24b, can activate a photoelectric implementation of chamber 22 via a conductor 26a. Smoke indicating signals can be received via conductor 26b at the control circuits 24.

Circuits 24 can process signals on line 26b to establish the presence of a potential or actual fire condition and couple that determination, via a wired or wireless communications medium 28, to an alarm system control unit 30. Circuits 24 can also include a local communications interface 24c, which might be implemented as a USB-type port, for use by an installer.

In the detector 10, larger airborne particles flow from port 12 to port 16 without being diverted into chamber 22. Hence, pollutants, such as dust particles and the like, will be excluded from chamber 22.

Figure 2:
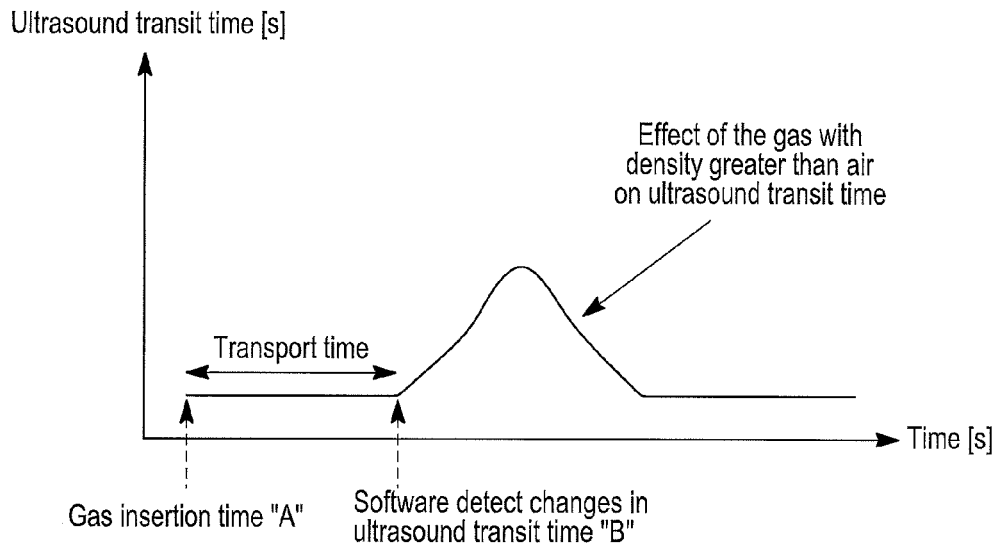
FIG. 2 is a graph which illustrates operation of aspects of the system of FIG. 1A.

Transport times, measured in a direction along the direction of ambient gas flow into the detector 10, or perhaps against the direction of such ambient gas flow, can be obtained using ultrasonic transducers transmitters/receiver 12-1, 12-2, coupled to control circuits 24. With respect to FIG. 2, with ambient air in the inflow pipe 12, measured directional ultrasonic transit times can be expected to be reasonably constant, within the measurement system accuracy, for constant environmental conditions.

When a sample gas G is injected into the pipe network P and inflow conduit 12, at insertion time A, the transit time will remain substantially constant until time B when the gas G enters the ultrasonic path between transducers 12-1, 12-2. When the transit time increases, at time B, due to increasing gas density, the difference B-A corresponds to the transport time. It is exclusive of smoke detector processing time.

Two different embodiments can be implemented. In a first, the aspirating smoke device 10 directly determines the ultrasound transit times and records when the flow medium inside the device is changed so as to establish the transport time. Alternately, an external device, for example a PC, such as 30, with dedicated software 30a, can be connected to the aspirating smoke detector 10 via interfaces 24c and 30b. The computer 30 receives, records, and processes the transit times, deduces when the flow medium changes, and can then establish the respective transport time.

As those of skill in the art will understand, embodiments hereof can be implemented using any of the aspiration detectors of the '457 patent, incorporated herein, or alternately, in publicly available aspiration detectors marketed by the assignee hereof as the SYSTEM SENSOR FAAST LT aspirating smoke detector.

Application software 30a can be provided to evaluate the ultrasound transit times. In this embodiment, the suggested procedure is:

Installer connects the inlets 12 of the device 10 to the pipe network P.

Installer connects the device 10 to the laptop 30.

Installer runs the software 30a that communicates with the device 10 and retrieves ultrasound transit times.

Installer inserts a gas G different from air in the sampling port of the pipe network being tested. Synchronization between the test software 30a and the gas insertion time can be implemented by another installer or with the help of time scheduling functionality of the test software 30a.

The test software 30a senses the transit times and responds to the time when the gas is arrived at the device 10. The interval, B-A, between the arrival time and the gas insertion time is the transport time.

Figure 3:
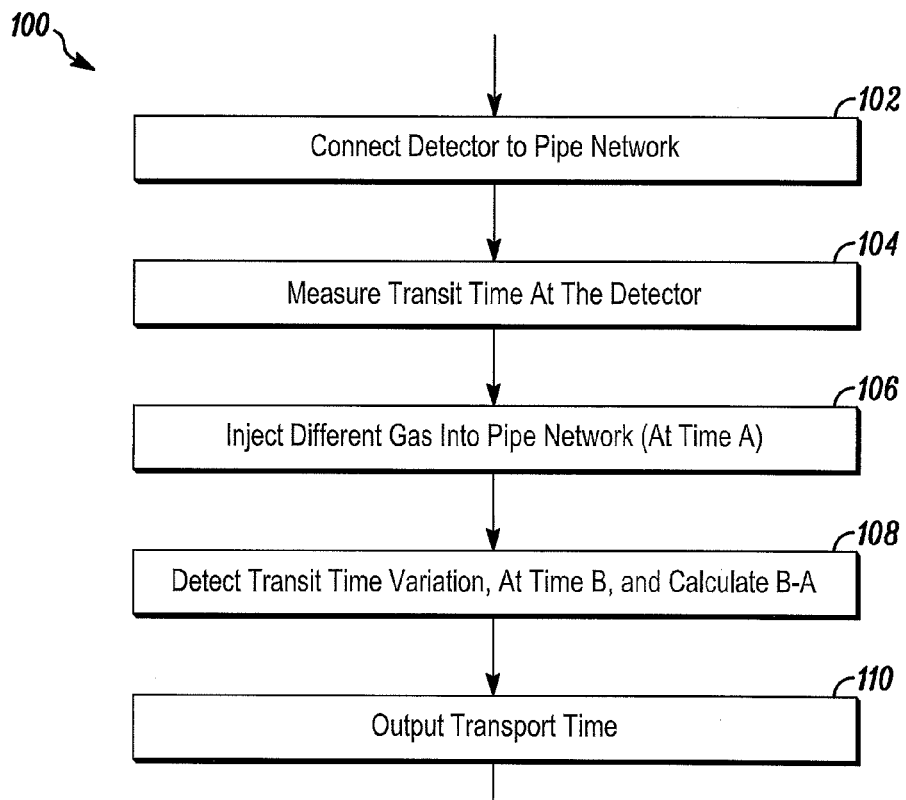
FIG. 3 is a flow diagram illustrating processing of the system of FIG. 1A.

FIG. 3 illustrates a flow diagram of a process 100. The detector is coupled to a conduit or pipe network as at 102. Transit time at the detector 10 is measured as at 104. A different gas can be injected into the conduit or pipe network as at 106. The time from injection of the gas G to a transit time change at the detector 10 is measured as at 108. The transport time can then be output as at 110.

While the above exemplary embodiments have been discussed in terms of using electro-acoustic processing to determine when the gas G has arrived at the detector 10, those of skill will recognize that other types of processing can be used. For example, electro-magnetic processing can be used. For example, if the opacity of air is different than the opacity of the gas G, optical readings can be made to determine when the gas G has arrived at the detector 10 to determine transport time. All such variations come within the spirit and scope hereof, without limitation.

From the foregoing, it will be observed that numerous variations and modifications may be effected without departing from the spirit and scope hereof. It is to be understood that no limitation with respect to the specific apparatus illustrated herein is intended or should be inferred. It is, of course, intended to cover by the appended claims all such modifications as fall within the scope of the claims. Further, logic flows depicted in the figures do not require the particular order shown, or sequential order, to achieve desirable results. Other steps may be provided, or steps may be eliminated, from the described flows, and other components may be added to or removed from the described embodiments.

The invention claimed is:

1. A method of measuring transport time comprising:
providing an ambient condition detector coupled to at least one sample inflow conduit;
measuring ultrasonic transit times through ambient air in the at least one sample inflow conduit;
injecting a different gas into the at least one sample inflow conduit at a first time;
continuing to measure the ultrasonic transit times through the ambient air in the at least one sample inflow conduit until a change in the ultrasonic transit times is detected at a second time; and
based on a difference between the first time and the second time determining the transport time.

2. A method as in claim 1 wherein providing includes coupling an aspirated detector to the at least one sample inflow conduit.

3. A method as in claim 1 which includes providing first and second spaced apart ultrasonic flow detectors in the at least one sample inflow conduit.

4. A method as in claim 3 which includes providing a programmable processor coupled to the ambient condition detector.

5. A method as in claim 4 which includes coupling executable instructions to the programmable processor to measure the ultrasonic transit times.

6. A method as in claim 5 wherein the programmable processor is one of internal to the ambient condition detector and attached to the first and second spaced apart ultrasonic flow detectors, or wherein the programmable processor is external to the ambient condition detector and coupled to the first and second spaced apart ultrasonic flow detectors.

7. A method as in claim 3 which includes measuring the ultrasonic transit times in at least one direction between the first and second spaced apart ultrasonic flow detectors.

8. A method as in claim 7 which includes measuring the ultrasonic transit times in a reverse direction between the first and second spaced apart ultrasonic flow detectors.

9. An apparatus for measuring transport time in an aspirated smoke detector comprising:

programmable control circuits coupled to first and second ultrasonic transducers; and pre-stored instructions, executed by the programmable control circuits, to measure and store flow transit times between the first and second ultrasonic transducers in at least one direction, wherein the pre-stored instructions determine a first time when a different gas is injected into a conduit, wherein the pre-stored instructions at least intermittently compare indicia of first stored transit times in ambient air to indicia of subsequently measured second transit times in the different gas, and, responsive to a detected difference therebetween, determine a second time, and wherein the pre-stored instructions determine the transport time by calculating a difference between the second time and the first time.

10. An apparatus as in claim 9 wherein the first and second ultrasonic transducers are coupled to the conduit, spaced apart from one another.

11. An apparatus as in claim 10 which includes an indicator indicative of when the different gas has been injected into the conduit.

12. An apparatus as in claim 11 wherein the indicator is stored and a second indicator is established in response to the detected difference.

13. An apparatus as in claim 9 wherein the second transit times are measured between the first and second ultrasonic transducers in a second direction.

14. An apparatus having an inflow pipe network comprising:

an aspirated smoke detector which is couplable to the inflow pipe network; and at least one sensor, carried at the aspirated smoke detector, to measure a predetermined ambient gas parameter, wherein the aspirated smoke detector stores a representation of the predetermined ambient gas parameter, receives a temporal indicator that a different gas is being injected into the inflow pipe network, with the aspirated smoke detector monitoring in real-time the predetermined ambient gas parameter being measured by the at least one sensor, and, responsive to a change therebetween, determines a transport time for the apparatus.

15. An apparatus as in claim 14 wherein the at least one sensor comprises one of an electro-acoustic sensor or an electro-magnetic sensor.

16. An apparatus as in claim 14 which includes executable instructions to store the representation of the predetermined ambient gas parameter, to monitor the predetermined ambient gas parameter, being measured, to compare the stored representation of the predetermined ambient gas to the real-time measured predetermined ambient gas parameter, and to determine the transport time by subtracting a time based indicium associated with a time that the different gas is being injected from a time based indicium associated with a time that a difference between the stored representation of the predetermined ambient gas parameter and the real-time measured predetermined ambient gas parameter is determined.

17. An apparatus as in claim 16 wherein the at least one sensor comprises at least one electro-acoustic transducer associated with a gas inflow path of the aspirated smoke detector.

18. An apparatus as in claim 17 which includes an interface to which a displaced computer is coupled, wherein the executable instructions reside in and are executed, at least in part, at the displaced computer.

* * * * *